United States Patent [19]

Siska et al.

[11] Patent Number: 4,946,288

[45] Date of Patent: Aug. 7, 1990

[54] DEW POINT ANALYZER

[75] Inventors: Paul Siska; Kewal K. Vij; Gyula Eisenbart, all of Calgary, Canada

[73] Assignee: Nova Husky Research Corporation, Calgary, Canada

[21] Appl. No.: 266,157

[22] Filed: Nov. 2, 1988

[51] Int. Cl.$^5$ ............................................. G01N 25/02
[52] U.S. Cl. ....................................... 374/20; 374/18; 374/28
[58] Field of Search .................................. 374/16–20, 374/27, 28; 73/23, 29

[56] References Cited

U.S. PATENT DOCUMENTS

| | | | |
|---|---|---|---|
| 2,733,594 | 2/1956 | Silverman | 374/18 |
| 3,623,356 | 11/1971 | Bisberg | 374/20 |
| 4,216,669 | 8/1980 | Harding | 374/20 |
| 4,240,284 | 12/1980 | Nguyen | 374/20 |
| 4,345,455 | 8/1982 | Hayes | 374/20 |
| 4,799,235 | 1/1989 | Bannell et al. | 374/18 |

FOREIGN PATENT DOCUMENTS

| | | |
|---|---|---|
| 3245184 | 8/1984 | Australia . |
| 813207 | 3/1981 | U.S.S.R. ................................ 374/20 |
| 1548976 | 7/1979 | United Kingdom . |

Primary Examiner—William A. Cuchlinski, Jr.
Assistant Examiner—Patrick R. Scanlon
Attorney, Agent, or Firm—Bernard, Rothwell & Brown

[57] ABSTRACT

The dew points of condensible hydrocarbon and water in a gas stream are determined independently in a single run by observing changes in intensity of light scattered from a mirror surface which is cooled to below both of the dew points. A decrease in intensity denotes the hydrocarbon dew point while an increase in intensity denotes the water dew point. The apparatus is simple and operates automatically. The mirror surface has a first polished and highly reflective portion and a second, roughened, less reflective portion. The intensity of scattered light is preferably monitored separately for each mirror portion.

25 Claims, 3 Drawing Sheets

DEW POINT ANALYZER

CROSS REFERENCE TO RELATED APPLICATION

This application is a continuation-in-part of U.S. Patent Application Ser. No. 903,971 filed Sept. 5, 1986 and now abandoned.

FIELD OF INVENTION

The present invention relates to the analysis of the dew point of condensible gases contained in gas streams, and provides a device suitable for the measurement of the dew points of hydrocarbon and of water vapour, and which can measure both dew points in a single run.

BACKGROUND OF THE INVENTION

In natural gas streams which are conveyed through pipelines there are generally strict limitations on the amount of water permitted therein, and on the dew point temperature of condensible hydrocarbons present therein. Unless such limitations are observed, serious pipeline problems can occur, including compressor malfunction and metering errors. Downtime due to repairs and cleaning can result in interruption of gas transmission. Accordingly, gas suppliers to a pipeline system are commonly obliged by contract to adhere to gas quality standards and to control and measure maximum water content and hydrocarbon dew point temperature at all pipeline inputs.

Gas pipeline operators routinely conduct independent dew point measurements to determine if the suppliers are complying with gas quality standards. Suppliers that fail to comply are at risk of being completely shut out of the gas pipeline system. If as a result of inaccurate dew point measurement, the pipeline operator wrongfully shuts the pipeline operator out of the system, the operator can be exposed to contractual liability. On the other hand, if the gas pipeline operator fails to detect accurately the presence of excessive water or condensible hydrocarbons, the safety of the gas pipeline system could be jeopardized. In particular, excessive water can cause freezing of safety relief valves and catastrophic damage to compressor blades.

In the North American natural gas industry, the dew points of hydrocarbon and water are typically measured by the Chandler dew point tester developed by the U.S. Bureau of Mines. The Chandler tester utilizes a highly reflective mirror placed in a flowing sample of natural gas stream. The mirror is cooled either by propane or carbon dioxide, depending upon the lowest mirror temperature desired, and the temperature at which the condensation is observed on the mirror is noted as the dew point. Condensation may be in the form of ice crystals when the water dew point of natural gas is being measured. The whole process of cooling the mirror, observation of the condensation and reading of the dew point temperature is manual. The requirement that an operator or technician physically attend at the measurement point is a distinct disadvantage, being labour intensive, a problem exacerbated by the location of pipeline facilities in increasingly remote areas. Furthermore, there is a practical limit to the frequency of such manual tests due to cost constraints. Additionally, because operators have differing abilities and perceptions, measurements with the Chandler tester are necessarily subjective and consequently can vary considerably.

Manual devices other than the Chandler tester have been proposed. For example, a manual device intended for measurement of water dew point is described in U.S. Pat. No. 2,733,594 (Silverman). Instead of using a highly reflective mirror as in the Chandler device, Silverman uses a collector having a large smooth area surrounding a roughened spot. According to Silverman, the roughened spot has peaks which tend to "seed" the vapour while this remains super-saturated over the smooth area. The moisture which thus condenses firstly on the roughened spot fill the pits and valleys of this rough surface which then becomes flooded and reflective as a result of the flooding. Silverman states that this condition allows an observer watching these surfaces to note "a great and marked increase in contrast" at the dew point. Thus, it is clear that in Silverman the "smooth" surface is not itself reflective or mirror-like as in the Chandler device. Furthermore, the dew point measured by Silverman cannot be the same as that conventionally measured by a smooth chilled mirror as in the Chandler device. Silverman makes it clear that condensation will occur on the roughened "seeding" surface at a higher temperature than that at which a dew or fog appears on the smooth surface. Also, Silverman's device is generally not useful for measuring water dew point in natural gas since such dew points usually fall below the freezing point of water. This results in condensation occurring in the form of ice crystals which would not give the flooding of the rough surface as required by the Silverman device. In addition, there is no suggestion in Silverman that his device could be used to detect the dew point temperature of hydrocarbons.

Proposals for automated water dew point measuring systems are contained in U.S. Pat. Nos. 4,216,669 (Harding), 4,345,455 (Hayes), and U.S.S.R. Pat. No. 813207. In each case, light reflected off an electrically cooled mirror surface is monitored by light detectors which are connected into logic circuits the operations of which are triggered by reduction in light reflected when moisture condenses on the mirror. The logic circuits operate to stabilize the mirror temperature at the dew point observed. Accordingly, such systems are inherently unsuitable for measurement of a second dew point of another substance. None of these patents suggests the capability of measuring hydrocarbon dew points nor do they indicate how dew points of two different gases could be distinguished.

Proposals have also been made in the past to provide for automated determination of hydrocarbon dew point in a natural gas stream. One such proposal appears in U.K. Pat. No. 1,548,976 (Schlumberger). As described therein, a frosted mirror is illuminated by a light source and light diffused by the mirror is detected by a photocell. The mirror is arranged to be cooled by a thermoelectric cooler and to be heated by a resistance heater. The mirror is progressively cooled as the test gas is passed through the chamber and at the dew point, the hydrocarbon condensation renders the mirror less diffusing and the photoelectric cell receives less light. The photoelectric cell is connected in an electrical circuit with the cooler and with the heater, and the circuit is arranged to re-heat the mirror as soon as hydrocarbons condense on the mirror; the mirror is constantly recycled close to the dew point allowing this to be measured. Again, this system could not be used to determine a second, lower, dew point of another substance, and the only use disclosed for this device is the detection of a single hydrocarbon dew point. There is no indication that the device could be used for detecting the dew point of water and no suggestion is made as to how to differentiate between the hydrocarbon and water dew points.

Another proposal for automated determination of the dew point temperature of light hydrocarbon in natural gas is described in U.S. Pat. No. 4,240,284 (Nguyen). Again, a frosted mirror is used and optical sensors monitor the light scattered by this mirror. As with Schlumberger, the patent is concerned with an automatic cycling system for heating the mirror and cooling it at controlled rates; this is intended to minimize error arising from the usual slow but continuous deposition of heavy hydrocarbons. There is again no provision for further reducing the mirror temperature after a dew point has been determined so this apparatus could not be used to determine a second, lower, dew point of another substance. There is reference in this patent to the possibility of modifying this system to determine the condensation point of water. However, this would involve the removal of the frosted mirror and the installation of a smooth mirror in its place. Additionally, Nguyen states that this modification might also require the rearrangement of the photocells in relation to the condensation mirror. Accordingly, it is apparent that with Nguyen, it would not be possible to determine the dew points of hydrocarbon and water in the same apparatus and especially in the same measuring run.

Despite the numerous proposals in the art for automated dew point monitors, by far the most common device in practical use is the Chandler dew point tester which has been used for decades. There remains a long felt and heretofore unfulfilled need for an automatic method and apparatus for the determination of the dew point of both hydrocarbon and water vapour in a gas stream in a single measuring run and for differentiating between the two.

SUMMARY OF THE INVENTION

The present invention not only distinguishes the dew points of hydrocarbon and water vapour but also determines them unambiguously in a single uninterrupted measuring run. In accordance with the present invention, in an automatic mode, the mirror is cooled with a thermoelectric cooler, its temperature is measured with a thermocouple, a thermistor, or a resistance temperature device (RTD) and the presence of condensation is detected by a light detection device disposed so as to measure the change in scattered light in a direction perpendicular to the mirror surface. Applicants have discovered that the measurement of scattered light in the perpendicular direction as an indicator of condensation has the advantage that the light scattering properties of condensed water and hydrocarbon can be used to distinguish between their respective dew points, and that it is possible to determine both dew points in a single device and in a single run. Hydrocarbons condense on the mirror surface as a thin film. Water can condense in the form of droplets or ice crystals, depending on the temperature. As used herein, the term "condense" in respect of water refers to the change of vapour phase to either the liquid or solid phase. The presence of a thin film, in the case of hydrocarbon condensation, reduces the intensity of scattered light in the perpendicular direction, whereas for water condensed droplets cause more light to scatter so that there is an increase in the light intensity in the perpendicular direction. Since the sense of the electrical signal caused by the change in scattered light due to condensation of hydrocarbon or water is of opposite polarity, the dew points of the respective components can be determined unambiguously. Unlike the automated systems described in prior patents referred to above, in accordance with the present invention, the mirror temperature is not automatically stabilized at the dew point to allow its determination; rather cooling of the mirror is continued until the second dew point is observed.

In order to take advantage of the different condensation properties of hydrocarbon and water to distinguish between their respective dew points, the mirror surface includes both a highly polished light reflecting portion and a roughened light scattering portion. In a preferred embodiment, the light detection device is such that it is capable of selectively detecting the light emanating from each portion of the mirror surface. In this embodiment, a charge coupled device (CCD) array is employed for this purpose. The mirror surface is focused on the CCD array by a lens such that separate elements of the array can independently detect the intensity of light emanating from different portions of the surface. In the absence of condensation, light falling at an angle to the mirror surface is substantially reflected by the polished surface and substantially scattered by the roughened surface. The CCD array is placed substantially perpendicularly above the mirror and the field of view is so adjusted that it picks up only the scattered component of light. In the absence of condensation the polished surface will be viewed by the CCD array as a substantially black surface whereas the rough surface will appear illuminated. When hydrocarbon condensation occurs on the surface of the mirror in the form of a thin film, the polished portion of the mirror does not change its reflecting property but the rough surface now becomes more reflective and the pixels of the CCD array looking at this surface register lower light intensity and their output falls from the white level towards the black level. In the case of water condensation, the scattering property of the rough surface does not change appreciably but the polished surface becomes substantially more scattering and the CCD pixels looking at this part of the mirror register an increase in light intensity with their output increasing toward the white level. By monitoring the CCD output as a function of temperature one can, therefore, not only determine the onset of condensation for each component in a single run, but can also determine in each case whether the condensate is hydrocarbon or water. Thus, the dew point temperature of each component can be determined unambiguously.

Once the dew point temperatures have been determined, this information can then be used to calculate the concentration of water in the gas stream sample and assure that this and the hydrocarbon dew point temperature are within the desired limits.

In another aspect, the present invention also includes a dew point detection device for carrying out the method of the invention. The device includes a gas sample-receiving chamber and a mirror. The surface of the mirror has a first portion which is polished to be highly reflective and a second portion which is roughened to be substantially light scattering, for the reasons discussed above. The roughened surface need not have peaks to provide seeding as required by Silverman.

Means are provided for controlling and measuring the temperature of the mirror surface. A window, transparent to light, is provided on a side of the chamber generally opposite the surface and a light beam source is arranged to direct a beam of light onto the surface at an oblique angle so that light scattered from the surface will pass out through the window. Scattered light detection means arranged on a path perpendicular to the light reflecting and scattering surface is also provided which preferably independently detects changes in intensity of light scattered by the polished and roughened portions of the surface passing through the window.

DESCRIPTION OF PREFERRED EMBODIMENT

Figure 1:
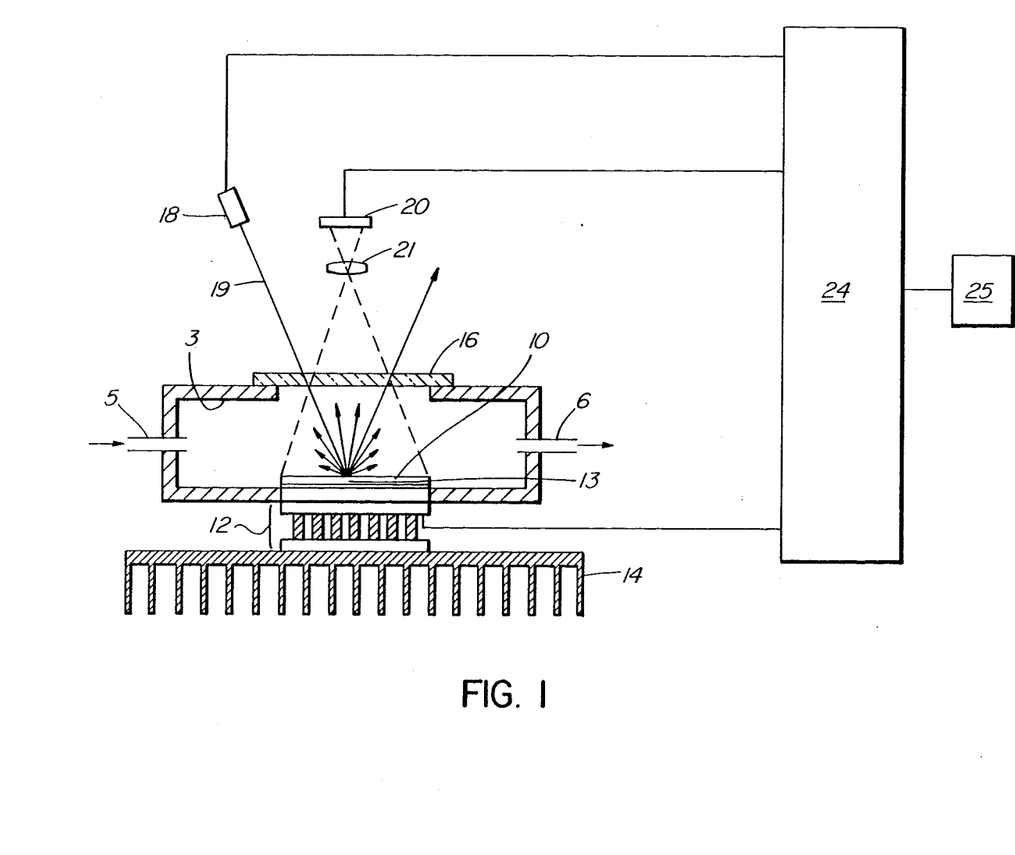
FIG. 1 is a schematic drawing of a dew point detection device constructed in accordance with one embodiment of the invention.

Referring to FIG. 1, a dew point detection device includes a zone comprised of an enclosed chamber 3 having an inlet 5 and an outlet 6 to permit a gas sample to be passed into and out of the chamber 3.

A planar mirror with surface 10 is located inside the chamber 3 in operative association with a cooling/heating unit 12, preferably a thermoelectric device. Cooling/heating unit 12 has associated therewith temperature sensor 13 which detects the temperature of the mirror surface 10. The unit 12 is also connected to a heat sink 14. The unit 12 is capable to cooling the mirror from ambient temperature (which may be 40° C.) down to at least −10° C., and preferably to −20° C. In the preferred embodiment the unit is capable of cooling the mirror down to −40° C.

In practice, it has been found that the sensitivity of the system to a decrease in the intensity of scattered light and hence the accuracy of determining the dew point for hydrocarbon in the gas stream is significantly improved if the surface 10 is roughened to increase the intensity of scattered light. However, such roughening of the surface decreases the sensitivity to water dew point determination. Accordingly, the surface 10 preferably comprises a combination of a polished and highly light reflective portion and a roughened light scattering second portion.

A light transparent window 16 is provided in a wall of chamber 3 on the side of the chamber opposite the mirror surface 10. A light beam source 18 is located externally of the chamber 3 to direct a light beam 19 onto the mirror surface 10 at an incident angle so that the reflected light from the mirror surface is out of the field of view of a light detecting device 20 and only the light scattered from the mirror surface is directed onto the light detecting device 20.

Light detection device 20 is located along a light transmittance path which extends perpendicularly to surface L 10, to detect light scattered in its field of view from this surface. Scattered light is focused onto device 20 by lens 21. The light detection device is of the form that it can selectively and independently detect the changes in light intensity scattered from each of the highly polished and roughened areas of surface 10. Preferably, the light detector device is a linear CCD array, having one group of pixels positioned to receive focused scattered light on the smooth highly-polished portion of surface 10 and one group positioned to receive focused scattered light on the roughened portion.

A micro-computer based data acquisition, data processor and control unit 24 is provided to acquire data from the light detection device 20 and to determine the onset of condensation. The unit 24 is also arranged to control the cooling/heating of the mirror surfaces 10 by switching the cooling/heating unit 12 to either cooling or heating mode. It may also control the output light intensity of light source 18 depending on the surface conditions of the light scattering mirror or to compensate for the effect of deposits or contaminants on the surface 10.

A unit 25 is provided either locally to display the dew point temperature and whether it is water or hydrocarbon condensing, or to provide appropriate telemetry signals for transmission of such information to a remote data gathering system.

OPERATION

In operation of the device of FIG. 1, a test gas sample is introduced into the chamber 3. The temperature of the surface 10 is varied by the cooling/heating unit 12 and is measured by the temperature sensor 13. A light beam 19 is directed onto the surface 10 and the light scattered in the field of view of the light detecting device 20 is monitored.

A change in intensity of the scattered light is employed as an indicator of the presence of condensation on the cooled surface. Since the condensation of hydrocarbon and water from the test gas stream produce opposite results in terms of the sense of the associated change in scattered light intensity, as described above, a clear differentiation can be made between the hydrocarbon and water dew points.

At the start of the measuring run, a sample stream of natural gas under test is introduced through the inlet so that the pressure of the gas inside the cell is the same as the line pressure and is maintained at substantially line pressure throughout the measuring run. The temperature of the mirror surface 10 is lowered progressively at a pre-determined and controlled rate by the unit 12 in a single run from a temperature above the dew points of both the hydrocarbon and water vapour contained in the gas sample to a temperature below both of said dew points. The rate of cooling is under the control of the micro-processor control unit 24. The data acquisition system 24 determines independently during such run the intensity of the light scattered from the highly reflective portion of mirror surface 10 and the roughened less reflective portion of mirror surface 10 in the absence of any condensation. The output of the CCD array 20 and the temperature of mirror surface 10 are monitored and recorded by the data acquisition system 24 at selected temperature intervals, namely at 0.5° C. intervals, as the mirror surface is cooled to the minimum temperature. After reaching the minimum temperature microprocessor control unit 24 puts the cooling/heating unit 12 into a heating mode to evaporate the condensate from mirror surface 10 and puts the data processor into dew point calculation mode. The recorded data of the CCD output for each temperature measurement, for each of the roughened and the polished mirror surface portions, is compared with the corresponding value of the previous measurement. Whenever the difference in these values changes by more than a pre-determined amount, the temperature of that measurement is taken as a dew point temperature. The data processor system 24 also determines the polarity of the signal change and indicates whether it is the hydrocarbon or water dew point temperature that has been reached. Both the dew point temperature and the component that has condensed are displayed on the display unit 25, or can be transmitted to a remote data gathering system.

One advantage of the use of light detecting device 20 that is capable of independently detecting the changes in light intensity scattered from each of the polished and roughened areas of surface 10 is that a false indication of the occurrence of condensation of one component due to "puddling" of a previously condensed component can be avoided. Puddling occurs when condensate coalesces on surface 10. Puddling, in the case of hydrocarbons, causes the thin film which has condensed to break into relatively thick puddles which increase the light scattering effect causing an increase in light intensity detected by light detection device 20. Because light detection device 20 can discriminate between the polished and the rough portions of mirror surface 10 and accordingly can indentify whether the changes in intensity are due to hydrocarbon or water condensation, the increase in light intensity due to puddling of the hydrocarbon is not misinterpreted as the onset of condensation of water vapour.

At the completion of the above described measuring run, a new measuring run can be initiated by a command from the control unit 24.

Figure 2:
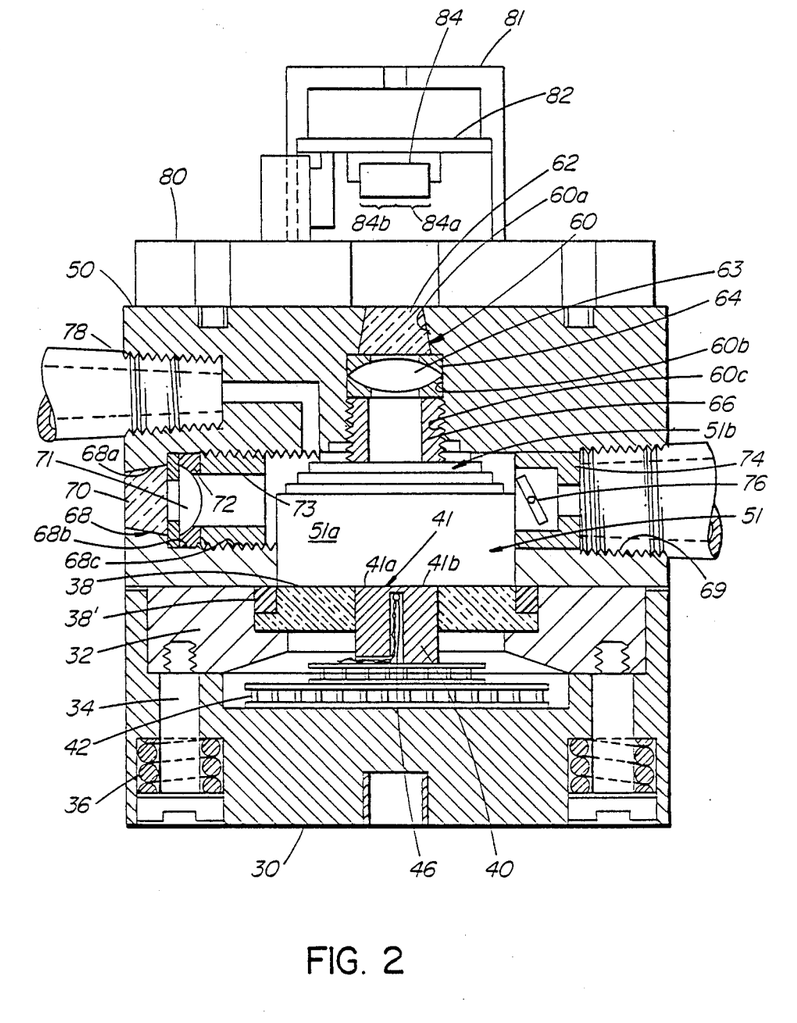
FIG. 2 is a partially schematic cross-section through a preferred embodiment of the device.

FIG. 2 shows the structure of a preferred form of the dew point detection device without the data acquisition and control system.

A base 30 of heat conductive metal, preferably aluminum, is provided with an outer recess holding a brass flange 32, the flange being firmly pulled into the recess by bolts 34 and springs 36. The flange 32 itself has an internal recess which receives an annular member 38 of heat insulating material such as polycarbonate, the centre of which holds a circular copper cylinder 40. The lower end of cylinder 40 is pressed against, and in good thermal contact with, the upper surface of a thermoelectric cooler 42 contained within an inner recess in base 30, the colder parts of cooler 42 being spaced from the parts 30 and 38 to avoid direct heat transfer from these parts to the cooler. The base 30 is in good thermal contact with a heat sink, not shown. The heat sink may be a finned thermal conductor, for example of aluminum, itself cooled by a fan. Alternatively, a heat sink similar to a small air conditioning device may be used.

The top 41 of cylinder 40, which is co-planar with the top of member 38, forms a circular mirror having two semi-circular side portions. A first side portion 41a is smooth and highly polished, and the second portion 41b is roughened. A suitable degree of roughness is that obtained by sand blasting and then subjecting the surface to a process such as that known as Ebonol C Black (trademark) which provides an oxide coating. Within the centre of cylinder 40 and separated from the mirror surface 41 by a thin wall is a thermistor device 46 having leads which pass through axial and radial bores in the cylinder 40. Base 30 houses a connector (not shown) for the leads to the thermistor device 46 and to the cooler 42.

The annular member 38 is held in place by an upper housing 50 having an internal chamber 51 with a main, lower cylindrical portion 51a, and an upper portion 51b within an inwardly sloping roof portion; both portions are co-axial and their axis is perpendicular to the plane of the mirror 41. The bottom of chamber portion 51a is defined by a cylindrical wall which rests on an o-ring 38' recessed into the outer edge of member 38. The roof portion is stepped to provide a series of alternating cylindrical surfaces and flat surfaces and which face member 38. This formation is designed to minimize internal reflections within the chamber. Stray light is also minimized by making the interior surface flat black. Preferably the housing material is aluminum and this is subjected to sand blasting and an anodizing treatment which produces a black oxide on the interior surface. The housing part 50 is thick walled so that the device can safely receive and maintain, in chamber 50, gas at pipeline pressure. The device is designed to receive and maintain gas at high pressure, for example, 1,000 psi for natural gas pipeline applications.

The upper portion 51b converges towards a bore 60 in the housing, co-axial with the chamber axis, and which includes an outer, inwardly diverging portion 60a, a central cylindrical cavity 60b, and a lower, screw threaded portion 60c. The portion 60a contains a window 62 of transparent plastics material such as polycarbonate which is firmly sealed within the bore, and which is in the form of a plug designed so that internal pressure increases the effectiveness of the seal between the window and housing. Portion 60b contains a converging lens 63 held by spacers 64 which are retained in place by hollow screw threaded member 66 engaging the threads of portion 60c.

At opposite sides of housing 50 radial bores 68 and 69 are provided which have a common axis perpendicular to that of the housing and located just below upper portion 51b. Radial bore 68 has an outer, inwardly diverging portion 68a, a central cylindrical cavity 68b, an an inner screw threaded portion 68c. The portion 68a contains a plug-like window 70 similar to window 62, and cavity 68b contains a converging lens 71 held by spacers 72 retained by hollow member 73 in portion 68c. Radial bore 69 has a cylindrical cavity containing a hollow cylindrical holder 74 having opposite sides recessed to receive pivot pins projecting from opposite sides of a flat circular mirror element 76 which has an inner surface angled downwardly towards mirror 41. The arrangement is such that a light source outside the housing can be arranged to direct a light beam through window 70 and lens 71 radially into the chamber, which beam is reflected by mirror 76 to meet mirror 41 at an oblique angle, for example, of about 45 degrees. This angle can be adjusted by rotating mirror 76 about its pivot pins. Light scattered from mirror 41 can pass out of the housing through lens 63 and window 62.

Housing 50 also includes a gas inlet port 78 which communicates with the upper chamber portion 51b. The bore 69 serves as a gas outlet port by virtue of leakage space which is provided between mirror element 76 and the holder 74. Both ports 78 and 69 are threaded to receive standard threaded pipe elements. The element engaging part 69 retains holder 74 in place Plate 80 is fixed to the top of housing 50, and supports a light sensor housing 81. This contains a mounting plate 82 carrying an array 84 of charge coupled devices (CCD) arranged to detect light scattered by mirror 41 in a substantially perpendicular direction and which has been focused by lens 63 through window 62. The lens 63 focuses an image of a representative linearly extending area of mirror 41 onto the CCD array, in such manner that a first part 84a of the array 84 can receive light scattered from a narrow, elongated portion of the polished surface portion 41a of mirror 41, and a second part 84b of the array can receive light scattered from the roughened surface portion 41b of mirror 41, both these portions being aligned. The two parts 84a and 84b of the array 84 are connected independently to a data acquisition and processing computer, which is also connected to the thermoelectric cooler 42 and the mirror thermocouple 46. The computer is arranged to monitor sequentially each of the elements (pixels) of the CCD array 84.

Figure 3:
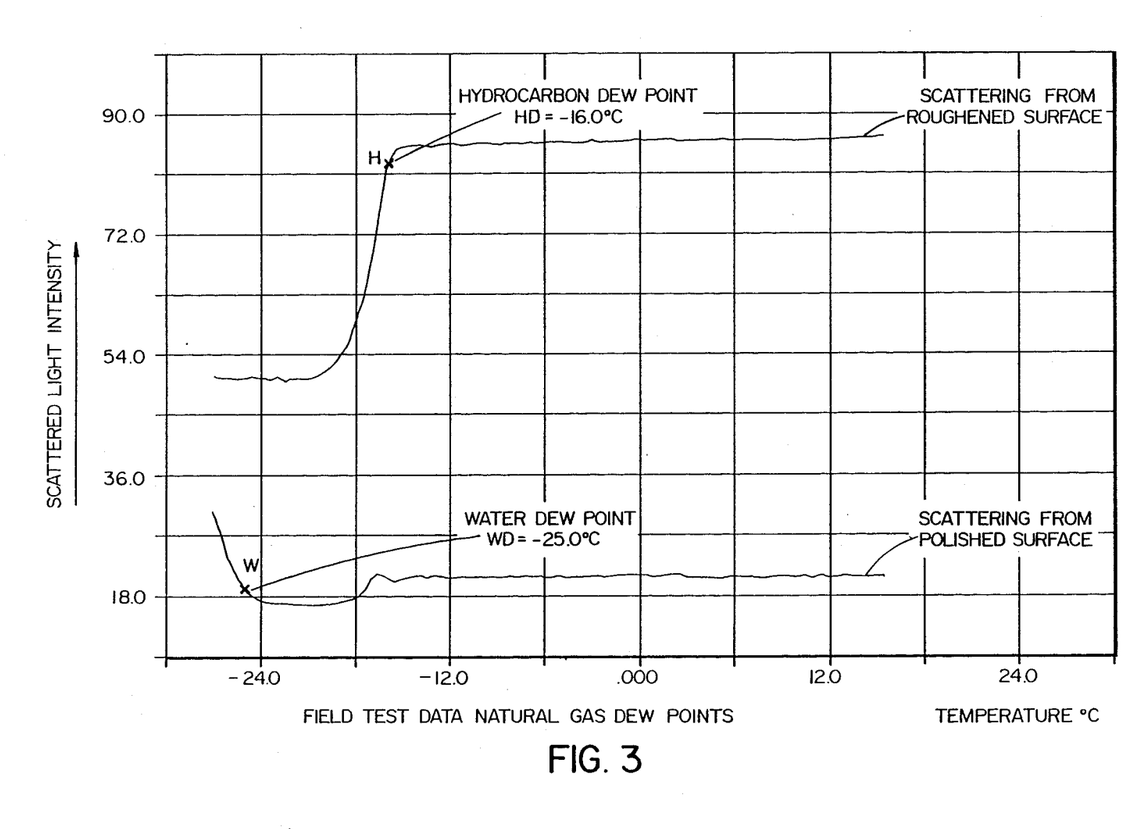
FIG. 3 is a graph showing results obtained when measuring the water and hydrocarbon dew points of a gas sample.

Operation of the device is similar to that described with reference to the first embodiment. The computer controls the cooling of mirror surface 41, and processes signals received from the thermistor 46 and from the CCD array 84. The computer averages the output for the pixels of each array part 84a and 84b separately. The computer displays on a monitor screen continuous indications of temperature intervals and of the average intensity of the scattered light received by the pixels of each of the CCD array parts 84a and 84b as the mirror surface 41 is cooled. A sample display obtained for a full cooling run is shown in FIG. 3. In contrast to some automated devices shown in prior patents referred to above, cooling is continued after the dew point of the first condensate has been reached until the second dew point has been determined.

As shown in FIG. 3, the bottom line shows the output from array 84a. The point (W) indicated as the water dewpoint shows the temperature (about $-25°$ C.) at which scattered light caused by ice crystals condensing on the polished mirror portion shows a sharp increase. The top line in FIG. 3 represents light scattered from the roughened portion of the mirror, and the hydrocarbon dewpoint (H) is recorded as the temperature (about $-16°$ C.) at which this scattered light shows a marked decrease. It will be apparent that with this system the two dew points are readily distinguishable and can be determined to an accuracy of about $\pm 1°$ C.

When used with natural gas samples, the conditions of water content and pressure are such that the water dew point will usually be below freezing point so that the water will condense as ice crystals. In contrast to some prior art proposals, this fact does not adversely affect operation.

The light beam source is shown as outside the chamber since the chamber is subjected to high pressure as discussed above. However, if the device is designed for use at low pressures then a light source within the chamber can be used. Also, in certain applications, it may be convenient to use fibre optics to transmit light into the chamber.

While the invention as described in FIGS. 1 and 2 has been schematically shown with the mirror horizontally disposed, in practice it has been found that the invention may be advantageously installed such that the mirror surface is vertically disposed. When vertically disposed, the adverse effect of puddling is minimized due to run off of excessive condensate.

The invention has been described as using two portions of a mirror surface, it will be understood that separate mirrors, one reflective and highly polished and one roughened and scattering, may be used. Separate light beams may be used for such separate mirrors.

While the invention has been described for use in sampling natural gas in pipeline applications, the invention is useful for measuring dew points in other applications such as dielectric gas in high voltage electrical utility transformers.

We claim:
1. A method for the independent determination of the dew points of hydrocarbon and of water in a gas stream in a single run, which comprises:
   providing a sample of the gas stream containing hydrocarbon and water vapours in a gas sample receiving chamber and causing the gas to contact a light reflecting and scattering surface having a first polished and highly reflective portion and a second, roughened, less reflective portion;
   shining a light beam onto said surface at an incident angle thereto such that, in the absence of condensation, the beam is substantially reflected by the first portion and substantially scattered by the second portion;
   cooling said surface while said gas sample is maintained in contact therewith, and said light beam is continued to be shone on to said light reflecting surface,
   obtaining, by light detecting means, electrical signals indicating the intensity of light scattered from both the first and second portions of the said surface, and monitoring said signals during said cooling step; and
   determining the dew point for said water vapour by recording the temperature of said surface when said signals indicate an increase in said intensity due to light scattering, and determining the dew point of hydrocarbon by recording the temperature of said surface when said signals indicate a reduction in intensity, the cooling being continued after determination of the first detected dew point and until both of said dew points have been determined.

2. The method of claim 1 wherein the intensity of light scattered by each of the polished and roughened portions of said surface is selectively monitored by the light detection means, and wherein the dew point for water is determined by recording the temperature of said surface when said signals indicate an increase in said intensity due to light scattering by water condensing on said polished and highly reflective portion and the dew point of hydrocarbon is determined by recording the temperature of said surface when said signals indicate a reduction in intensity due to condensation of hydrocarbons on said roughened and less reflective portion.

3. A method according to claim 1 wherein the pressure of the sample is such that condensation of water vapour occurs as ice crystals.

4. A method according to claim 1 including the step of focusing the light scattered from said surface so as to image said first and second portions of said surface onto said detection means and independently monitoring the intensity of scattered light for each of said portions.

5. A dew point detection device for determining the dew points of hydrocarbon and of water in a gas stream comprising:
   a gas sample-receiving chamber;
   a light reflecting and light scattering surface located in said chamber, said surface having a first portion which is polished to be highly reflective and a second portion which is roughened to be light scattering;
   means for changing the temperature of said surface and for monitoring the temperature of said surface;
   a light beam source arranged to direct a beam of light onto both portions of said surface at an oblique angle while cooling said surface so that light from the beam is scattered and reflected from said surface; and light detection means located along a light transmittance path generally perpendicular to said surface for detecting only light scattered by both portions of said surface and producing output signals corresponding to the intensity of light scattered from both portions of said surface and connected into circuit means capable of registering both an increase in light scattered from the first portion of said surface as an indication of water dew point, and a decrease in light scattered from the second portion of said surface as an indication of hydrocarbon dew point; and said temperature changing means being arranged to continue cooling of said surface after the first dew point has been indicated and until both dew points have been indicated.

6. The apparatus of claim 5 wherein the scattered light detection means is constructed to detect selectively light scattered from each of said portions of said surface.

7. The apparatus of claim 6 including a data processing and control means to control the intensity of the light beam source in response to the surface conditions of the said surface.

8. A device according to claim 6, wherein the light detection means comprises an array of light detecting elements and a lens which focuses light scattered from said surface so as to image said first portion of said surface onto a first part of said array and said second portion of said surfaces onto a second part of said array.

9. A device according to claim 8, wherein each element of said array is separately connected to said circuit means, and said circuit means include recording means connected to said temperature monitoring means and to output signal monitoring means for recording the temperature of said surface when said output signals indicate an increase in light scattered from the first portion of said surface and a decrease in light scattered from the second portion of said surface; and said recording means independently records the output signals of each part of said array.

10. A device according to claim 8, wherein said array is an array of charge coupled devices.

11. A device according to claim 5, wherein said chamber is provided within a thick walled pressure resistant housing capable of receiving and maintaining gas at high pressure, said chamber being generally cylindrical and surrounding an axis coincident with and perpendicular to a center of said surface; and wherein said light beam source includes a lens arranged to direct a beam of light across said chamber substantially perpendicular to said axis, and also includes a mirror disposed so as to reflect said beam on to said surface at an oblique angle thereto.

12. A device according to claim 11, wherein said chamber includes a main, lower cylindrical portion co-axial with said axis, and an inwardly sloping roof portion which is stepped to minimize internal reflections, all internal surfaces of said housing having a light absorbing surface.

13. A method for the determination of dew points of hydrocarbon and of water present in a gas stream, comprising:

(a) providing a chamber for receiving a gas sample, within which chamber is located a highly lightreflective first surface and a roughened, less reflective, light-scattering second surface;

(b) providing light detecting means positioned opposite said first and second surfaces for detecting light scattered by said surfaces, wherein said light detecting means provides an electrical signal corresponding to the intensity of light scattered by said surfaces;

(c) introducing into said chamber a sample of a gas stream containing hydrocarbon and water vapors, so as to place the sample in contact with said first and second surfaces between said surfaces and said light detecting means;

(d) shining light onto both said surfaces at an incident angle thereto such that, in the absence of condensation, said light is reflected by the first surface away from said detecting means, and said light is scattered by the second surface and detectable by said detecting means;

(e) monitoring the electrical signal of the detecting means while said light is shining on said surfaces;

(f) cooling said surfaces during a single measuring cycle through both dew points of hydrocarbon and water in the sample, said cooling taking place while said surfaces are at the same temperature as each other and while said gas sample is maintained in contact with said surfaces and said light is shining on said surfaces and while monitoring the electrical signal provided by said detecting means; and (g) determining the dew point for water by recording the temperature of said surfaces when said signal indicates an increase in light scattering intensity, and determining the dew point of hydrocarbon by recording the temperature of said surfaces when said signal indicates a reduction in intensity of scattered light.

14. The method of claim 13 wherein said surfaces are cooled in step (f) from a temperature of about $+40°$ C. to a temperature of about $-10°$ C.

15. The method of claim 13 wherein said surfaces are cooled in step (f) from a temperature of about $+40°$ C. to a temperature of about $-20°$ C.

16. The method of claim 13 wherein said surfaces are cooled in step (f) from a temperature of about $+40°$ C. to a temperature of about $-40°$ C.

17. In a method of determining the dew points of hydrocarbon and water in a gas sample of the type providing a mirrored surface, cooling the surface with the gas sample in contact with it at least until a constituent of the gas sample condenses on the surface, directing light onto the surface and measuring the intensity of light scattered by the surface while cooling the surface to determine the dew point of a constituent, improvements in the method allowing automatic and independent measurement of the dew points of both hydrocarbon and water in a single measuring cycle, comprising:

(a) providing the mirrored surface with two separate portions, a first highly reflective portion and a second roughened less reflective portion;

(b) continuing the cooling of said surface through both dew points of the water and hydrocarbon in the single measuring cycle; and (c) measuring the intensity of light scattered by each of the separate portions of the mirrored surface during the single measuring cycle so as to independently determine the dew points of both water and hydrocarbon in the single measuring cycle.

18. The method of claim 17 wherein said surface is cooled in step (b) from a temperature of about +40° C. to a temperature of about −10° C.

19. The method of claim 17 wherein said surface is cooled in step (b) from a temperature of about +40° C. to a temperature of about −20° C.

20. The method of claim 17 wherein said surface is cooled in step (b) from a temperature of about +40° C. to a temperature of about −40° C.

21. The method of claim 17 wherein intensity of scattered light is measured in step (c) of each separate portion of the mirrored surface independently.

22. An apparatus for the determination of dew points of hydrocarbon and of water present in a gas stream, comprising:
- (a) a chamber for receiving a gas sample, within which chamber is located a highly light-reflective first surface and a roughened, less reflective, light-scattering second surface;
- (b) a light detecting means positioned opposite said first and second surfaces for detecting light scattered by said surfaces, wherein said light detecting means provides an electrical signal corresponding to the intensity of light scattered by said surfaces;
- (c) means for introducing into said chamber a sample of a gas stream containing hydrocarbon and water vapors, so as to place the sample in contact with said first and second surfaces between said surfaces and said light detecting means;
- (d) means for shining light onto both said surfaces at an incident angle thereto such that, in the absence of condensation, said light is reflected by the first surface away from said detecting means and said light is scattered by the second surface and detectable by said detecting means;
- (e) means for monitoring the electrical signal of the detecting means while said light is shining on said surfaces;
- (f) means for cooling said surfaces during a single measuring cycle through both dew points of hydrocarbon and water in the sample, wherein the cooling means cools said surfaces while said surfaces are at the same temperature as each other and while said gas sample is maintained in contact with said surfaces and while monitoring the electrical signal provided by said detecting means; and
- (g) means for recording the temperature of said surfaces when said signal indicates an increase in light scattering intensity so as to determine the dew point for water in said sample, and for recording the temperature of said surfaces when said signal indicates a reduction in intensity of scattered light so as to determine the dew point of hydrocarbon in said sample.

23. The apparatus of claim 22 wherein the cooling means cools said surfaces during a single measuring cycle from a temperature of about +40° C. to a temperature of about −10° C.

24. The apparatus of claim 22 wherein the cooling means cools said surfaces during a single measuring cycle from a temperature of about +40° C. to a temperature of about −20° C.

25. The apparatus of claim 22 wherein the cooling means cools said surfaces during a single measuring cycle from a temperature of about +40° C. to a temperature of about −40° C.

* * * * *